United States Patent [19]

Masaki et al.

[11] Patent Number: 5,349,050

[45] Date of Patent: * Sep. 20, 1994

[54] PEPTIDES, AND ANTIDEMENTIA AGENTS CONTAINING THE SAME

[75] Inventors: Mitsuo Masaki, Chiba; Masaki Uehara; Kenji Hirate, both of Saitama; Yoshikazu Isowa, Tokyo; Yoshiaki Sato, Tokyo; Yoshiharu Nakashima, Tokyo, all of Japan

[73] Assignees: Nippon Chemiphar Co., Ltd.; Fujirebio Kabushiki Kaisha, both of Tokyo, Japan

[ * ] Notice: The portion of the term of this patent subsequent to May 12, 2009 has been disclaimed.

[21] Appl. No.: 838,140

[22] Filed: Feb. 18, 1992

Related U.S. Application Data

[62] Division of Ser. No. 509,950, Apr. 16, 1990, Pat. No. 5,112,947.

[30] Foreign Application Priority Data

| Apr. 15, 1989 | [JP] | Japan | 1-95917 |
| Apr. 15, 1989 | [JP] | Japan | 1-95918 |
| Apr. 15, 1989 | [JP] | Japan | 1-95919 |
| Apr. 15, 1989 | [JP] | Japan | 1-95920 |
| Apr. 15, 1989 | [JP] | Japan | 1-95921 |
| Apr. 15, 1989 | [JP] | Japan | 1-95922 |

[51] Int. Cl.$^5$ .............. A61K 31/34; A61K 31/02; C07K 5/10; C07K 7/06
[52] U.S. Cl. .............. 530/330; 530/315; 530/329
[58] Field of Search .............. 530/329, 330; 514/17, 514/18

[56] References Cited

U.S. PATENT DOCUMENTS 5,112,947 5/1992 Masaki et al. .............. 530/329
5,180,712 1/1993 Isowa et al. .............. 530/329

FOREIGN PATENT DOCUMENTS 0354820 2/1990 European Pat. Off. .

OTHER PUBLICATIONS

Burbach, et al. Sci vol. 221, pp. 1310–1312.

Primary Examiner—Lester L. Lee
Assistant Examiner—S. G. Marshall
Attorney, Agent, or Firm—McAulay Fisher Nissen Goldberg & Kiel

[57] ABSTRACT

Disclosed is a novel peptide having one of the formulae:

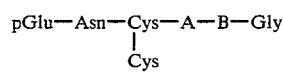

(A and B are the amino acids: wherein
if A is D- or L-Pro, B is Hat or Cit;
if A is D-Pro, B is D-Arg, and
if B is D- or L-Arg, A is Sat, Pip, Aze or Arg)
Asn-A-L- (D-)Pro-Arg- (Gly)n (A is Set, Thr or Ala, n is 1 or 0)
A-Ser-Pip-Arg (A is Pro-Asn-, Asn- or Pro-)

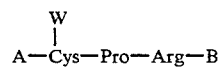

(A is cyclopentylcarbonyl, Pro or pGlu; B is Gly or β-Ala, W is a hydrogen atom or a group having the formula:
or a peptide having the formula:

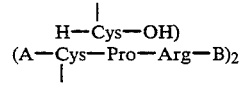

wherein A and B have the same meanings as mentioned above, respectively
pGlu-Asn-Ser-A-B-(Gly)n (A is Aze, D- or L-Pro, Pip or Sat, B is D- or L-Arg, Cit, Hat, Lys or Orn, n is 1 or 0) and
Pro- (Ash)m-Set-L- (D-)Pro-Arg- (Gly) n (m and n are independently 0 or 1)
their functional derivatives, and pharmaceutically acceptable salts thereof.

2 Claims, No Drawings

PEPTIDES, AND ANTIDEMENTIA AGENTS CONTAINING THE SAME

This is a division of application Ser. No. 07/509,950, filed Apr. 16, 1990 now U.S. Pat. No. 5,112,947.

BACKGROUND OF THE INVENTION

1. Field of the Invention

The present invention relates to novel peptides having a hoottopic effect and being useful as medicines, particularly as antidementia agents.

2. Description of Prior Art

Vasopressin has been previously known as a compound having a hoottopic effect, i.e., intelligence developing effect. Recently, it has been reported that peptides seemingly corresponding to a vasopressin fragment, for example, those having the following formulae:

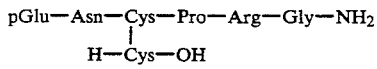

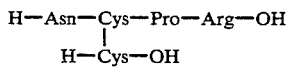

have such a nootropic effect as that of vasopressin in *Science*, 221, pp.1310–1312 (1983) and *Brain Research*, 371, 17(1986).

Further, there is also reported that a peptide having the following formula:

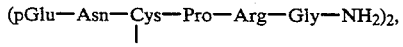

has a nootropic effect in Japanese Patent Provisional Publication No.59(1984)-93036.

SUMMARY OF THE INVENTION

It is an object of the present invention to provide new peptide derivatives which are superior in the nootropic effect to the known vasopressin as well as to the known peptides corresponding to vasopressin fragments.

The present invention provides a novel peptide having the formula (I):

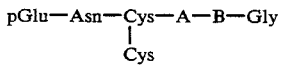

wherein A and B represent the amino acids; wherein
in the case that A is D- or L-Pro, B is Hat or Cit;
in the case that A is D-Pro, B is D-Arg; and
in the case that B is D- or L-Arg, A is Sar, Pip, Aze or Arg,
its functional derivative, and a pharmaceutically acceptable salt thereof.

Further, the invention provides an antidementia agent containing, as a pharmaceutically active component, an effective amount of the peptide having the above formula (I), its functional derivative or a pharmaceutically acceptable salt thereof and a pharmaceutically acceptable carrier or diluent.

The invention also provides a novel peptide having the formula (II):

Asn-A-L-(D-)Pro-Arg-(Gly)n  (II)

wherein A is Set, Thr or Ala, n is 1 or 0, its functional derivative, and a pharmaceutically acceptable salt thereof.

Further, the invention provides an antidementia agent containing, as a pharmaceutically active component, an effective amount of the peptide having the above formula (II), its functional derivative or a pharmaceutically acceptable salt thereof and a pharmaceutically acceptable carrier or diluent.

The invention further provides a novel peptide having the formula (III):

A-Ser-Pip-Arg  (III)

wherein A is Pro-Asn-, Ash- or Pro-, its functional derivative, and a pharmaceutically acceptable salt thereof.

Further, the invention provides an antidementia agent containing, as a pharmaceutically active component, an effective amount of the peptide having the above formula (III), its functional derivative or a pharmaceutically acceptable salt thereof and a pharmaceutically acceptable carrier or diluent.

The invention provides a novel peptide having the formula (IV):

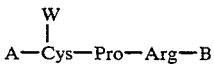

wherein
A is cyclopentylcarbonyl, Pro or pGlu; B is Gly or β-Ala; W represents a hydrogen atom or a Group having the formula (V):

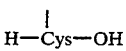

or a peptide having the formula (VI):

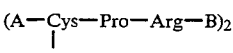

wherein A and B have the same meanings as mentioned above, respectively, its functional derivative, and a pharmaceutically acceptable salt thereof.

Further, the invention provides an antidementia agent containing, as a pharmaceutically active component, an effective amount of the peptide having the above formula (IV), its functional derivative or a pharmaceutically acceptable salt thereof and a pharmaceutically acceptable carrier or diluent.

The invention further provides a novel peptide having the formula (VII):

pGlu-Asn-Ser-A-B-(Gly)$_n$  (VII)

wherein A is Aze, D- or L-Pro, Pip or Sat, B represents D- or L-Arg, Cit, Har, Lys or Orn, n is 1 or 0, its functional derivative, and a pharmaceutically acceptable salt thereof.

Further, the invention provides an antidementia agent containing, as a pharmaceutically active component, an effective amount of the peptide having the above formula (VII), its functional derivative or a pharmaceutically acceptable salt thereof and a pharmaceutically acceptable carrier or diluent.

The invention further provides a novel peptide having the formula (VIII):

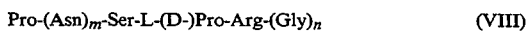

Pro-(Asn)$_m$-Ser-L-(D-)Pro-Arg-(Gly)$_n$     (VIII)

wherein m and n are independently 0 or 1, its functional derivative, and a pharmaceutically acceptable salt thereof.

Further, the invention provides an antidementia agent containing, as a pharmaceutically active component, an effective amount of the peptide having the above formula (VIII), its functional derivative or a pharmaceutically acceptable salt thereof and a pharmaceutically acceptable carrier or diluent.

The above-mentioned peptides, their functional derivatives, and their pharmaceutically acceptable salts show prominent a nootropic effect in passive avoidance tests using rats, and are prominently effective as active component of pharmaceutical agent for prevention or treatment of senile dementia (Alzheimer's dementia), cerebrovascular dementia and other dementia diseases.

DETAILED DESCRIPTION OF THE INVENTION

The peptides and peptide derivatives having the above formulae of the present invention are compounds of which amino acid sequences are different from those of the aforementioned known peptides.

The word of "functional derivatives" of the peptides and peptide derivatives in the present specification means the following derivatives:

a) N-acyl derivatives having N-acyl group(s); wherein N-acyl group is derived from an aliphatic carboxylic acid having 1 to 6 carbon atoms, preferably one derived from acetic acid; the N-acyl group can be expressed by —NHCOR (wherein R is an alkyl group having 1–5 carbon atoms), b) derivatives having groups in the form of amides, or monoalkyl or dialkyl substituted-amides having alkyl chain(s) of 1 to 6 carbon atoms; which can be expressed by —CONH$_2$, —CONHR, and —CONR$_2$ (wherein R is an alkyl group having 1–6 carbon atoms),
and c) derivatives having groups in the form of esters derived from alcohol having 1 to 18 carbon atoms, preferably those derived from an aliphatic alcohol having 1 to 6 carbon atoms; which can be expressed by —COOR (wherein R is an alkyl group having carbon 1–18 atoms, preferably 1–6 carbons).

As the examples of pharmaceutically acceptable salts of the peptides and the peptide derivatives of the invention, acid addition salts and basic salts such as alkali metal salts and ammonium salts can be mentioned. Examples of such acid addition salts include salts of inorganic acids (e.g., hydrochloric acid, sulfuric acid and phosphoric acid) or of organic acids (e.g., acetic acid, propionic acid, citric acid, tartaric acid, maleic acid, oxalic acid and methanesulfonic acid). Examples of basic salts include sodium salt, potassium salt, and triethylamine salts. In the specification, amino acids, peptides, protecting groups and solvents are described by abbreviations commonly used in the field of chemistry, or abbreviations recommended by the IUPAC-IUB Commission on Biochemical Nomenclature. For example, the following symbols are used in the specification. The amino acids should be construed to be of the L-type, unless specific description with respect to optical configuration is given.

β-Ala : β-alanine
Arg : arginine
Ala : alanine
Asn : asparagine
Aze : azetidine-2-carboxylic acid
Cit : citrulline
Cys : cysteine
Gly : glycine
Har : homoarginine
Lys : lysine
Orn : ornithine
pGlu : pyroglutamic acid
Pip : pipecolic acid
Pro : proline
Sar : sarcosine
Ser : serine
Thr : threonine
Boc : t-butoxycarbonyl
Z : benzyloxycarbonyl
Fmoc : 9-fluorenylmethoxycabonyl
Bu$^t$ : t-butyl
Mbs : p-methoxybenzenesulfonyl
MBzl : p-methoxybenzyl
Acm : acetamidomethyl
Scm : S-carbomethoxysulfenyl
Mtr : 4-methoxy-2,3,6-trimethylbenzenesulfonyl
NO$_2$ : nitro
Bzl : benzyl
OBzl : benzyl ester
OSu : N-hydroxysuccinimide ester
DCC : N,N'-dicyclohexylcarbodiimide
DCUrea : N,N'-dicyclohexylurea
DIC : N,N'-diisopropylcarbodiimide
HOBt : 1-hydroxybenzotriazole
Et$_3$N : triethylamine
Trt : trityl
NMM : N-methylmorpholine
TFA : trifluoroacetic acid
MSA : methanesulfonic acid
AcOEt : ethyl acetate
AcOH : acetic acid
THF : tetrahydrofuran
DMF : N,N-dimethylformamide
MeOH : methanol The compounds of the present invention can be prepared by the methods conventionally employed in peptide chemistry. For example, the peptides can be prepared by those processes described in Schröder and Lübke, *The Peptides*, Vol. 1, Academic Press, New York, 1965, and Nobuo Izuraiya et al., *Fundamental and Experiment of Peptide Synthesis*, Maruzen, Tokyo, 1985, and can be prepared by either the solution synthesis or the solid synthesis.

Examples of the methods for formation of the peptide bonds include azide method, acid chloride method, symmetrical anhydride method, mixed anhydride method, carbodiimide method, carbodiimido-additive method, activated ester method, carbonyldiimidazole method, oxidation-reduction method, and the one employing a Woodward reagent K.

In the synthesis of peptide, the cystine moiety which is an amino acid forming the peptide of the invention can be formed by employing a cystine derivative or by converting a cysteine moiety of the peptide chain into a cystine moiety after the formation of the peptide chain by the conventional method.

Before carrying out the coupling reaction, carboxyl group, amino group, guanidino group, hydroxyl group, mercapto group and the like which do not participate in the reaction can be protected, and those which participate in the coupling reaction can be activated, both by the methods well known in the art.

Examples of the protecting groups for the carboxyl group include ester-forming groups such as methyl, ethyl, benzyl, p-nitrobenzyl, t-butyl and cyclohexyl.

Examples of the protecting groups for the amino group include benzyloxycarbonyl, t-butoxycarbonyl, isobornyloxycarbonyl, and 9-fluorenylmethyloxycarbonyl.

Examples of the protecting groups for the guanidino group include nitro, benzyloxycarbonyl, tosyl, p-methoxybenzenesulfonyl and 4-methoxy-2,3,6-trimethylbenzenesulfonyl.

Examples of the protecting groups for the hydroxyl group include t-butyl, benzyl, tetrahydropyranyl and acetyl.

Examples of the protecting groups for the mercapto group include trityl, acetamidomethyl, benzyl, p-methoxybenzyl and 3-nitro-2-pyridinesulfenyl.

Examples of the activated forms of carboxyl group include symmetrical anhydride, azide and active ester (ester with alcohol e.g., pentachlorophenol, 2,4-dinitrophenol, cyanomethyl alcohol, p-nitrophenol, N-hydroxy-5-norbornene-2,3-dicarboxyimide, N-hydroxysuccinimide, N-hydroxyphthalimide and 1-hydroxybenzotriazol). An example of the activated amino group is amide phosphate.

The reaction is generally carried out in a solvent such as chloroform, dichloromethane, ethyl acetate, N,N-dimethylformamide, dimethylsulfoxide, pyridine, dioxane, tetrahydrofuran, water, methanol and mixture of these solvents.

The reaction temperature may be in the range of approx. $-30°$ C. to $50°$ C., which is generally employed for the reaction.

The reactions for removing the protecting group of the peptide of the invention may differ depending on the kind of the protecting group, but it should be the one which is able to release the protecting group without giving any influence to the peptide bonding.

The protecting group can be removed by acid treatment, for example, treatment with hydrogen chloride, hydrogen bromide, hydrogen fluoride, methanesulfonic acid, trifluoromethanesulfonic acid, trifluoroacetic acid and mixture of these acids. Further, the reduction with sodium metal in liquid ammonia or catalytic reduction over palladium-carbon can be employed. In performing the reaction for removing the protecting group by the above acid treatment, addition of cation scavenger such as anisole, phenol and thioanisole is advantageously adopted.

After the reaction is complete, the prepared peptide of the present invention can be recovered by the conventional process for purification of peptides, for example, extraction, partition, reprecipitation, recrystallization or column chromatography.

Further, the peptides of the present invention can be converted into their functional derivatives or their pharmaceutically acceptable salts as described above in the conventional manner.

The compounds of the invention show a strong hoot-topic effect in passive avoidance tests using rats as described hereinafter.

The peptides and peptide derivatives of the present invention are effective to the following diseases, and be employed for prevention or treatment thereof: senile dementia (Alzheimer's dementia), cerebrovascular dementia, and demntia based on Alzheimer's disease, Pick's disease, Huntington's disease, Creutzfeldt-Jakob disease, Parkinson's disease and cerebellar myelic denatured disease.

The peptides of the invention have an extremely low toxicity, and cause no death even by administration at an extremely higher dose than its effective dose.

The peptides of the invention may be administered in the form of the peptides of the above-mentioned formulae, their functional derivatives or salt thereof. No matter their forms are, the dose as amount of the peptides of the above-mentioned formulae, is preferably in the range of 0.1 ng/day to 1 mg/day. In the case of parenteral administration and nasal administration, the dose preferably is in the range of 0.1 ng/day to 100 $\mu$g/day. In the case of oral administration and rectal administration, it is preferable that the dose should be 10 to 100 times to that of the parenteral administration. The peptide of the invention is mainly administered parenterally (e.g., intravenous or hypodermic injection, intracerebroventricular or intraspinal administration, nasal administration and rectal administration). It can be also administered orally depending on the case.

The peptides of the invention can be incorporated into pharmaceutical compositions in the form of injection liquid, suppository, powder, collunarium, granule and tablets. The peptides of the invention can be preserved as a physiological saline solution or can be freeze-dried in an ample after addition of mannitol or sorbitol and is melted when it is used for administration.

Examples of the invention are set forth hereinafter.

In each example, the eluents used for a thin-layer chromatography were as follows. As for the solid phase, TLC Plate Silica Gel 60F$_{254}$ by Merck Co., Ltd. was used.

$Rf^1$: choroform-methanol - acetic acid -water (80:20:2.5:5) lower layer $Rf^2$: choroform-methanol-water (70:30:5)

$Rf^3$: n-butanol -acetic acid-water (2:1:1)

Further, purification by a high-performance liquid chromatography was carried out using the following materials:

Column: $\mu$Bondapak C$_{18}$ 1.9$\times$15

Mobile phase: A) 0.05 % TFA, B) acetonitrile

The preparation of peptide in solid phase was carried out by the process in which the peptide chain was extended step by step in the following manner using 1 g (0.24 mmol NH$_2$/g) of 2,4 -dimethoxybenzhydrylamine resin [*J. Org. Chem.*, 52 (1987), 1197].

| reagent, solvent | period (minute) $\times$ times |
|---|---|
| Coupling Process | |
| 1. DMF | 1 $\times$ 3 |
| 2. Fmoc-amino acid + HOBt + DIC (each of them are same amount.)-DMF | 120 |
| 3. DMF | 1 $\times$ 3 |
| 4. iso-propanol | 1 $\times$ 3 |
| 5. CH$_2$Cl$_2$ | 1 $\times$ 3 |
| N$^\alpha$-Deprotection Process | |
| 6. DMF | 1 $\times$ 3 |
| 7. 20% piperidine-DMF | 1 |

| reagent, solvent | period (minute) × times |
| --- | --- |
| 8. 20% piperidine-DMF | 20 |
| 9. DMF | 1 × 3 |
| 10. CH$_2$Cl$_2$ | 1 × 3 |

The coupling reaction was confirmed by Kayser test. If necessary, the above steps 1–5 were repeated.

EXAMPLE 1

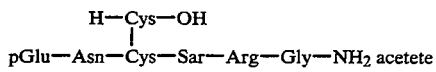

pGlu—Asn—Cys—Sar—Arg—Gly—NH$_2$ acetete

Fmoc-Gly-OH-resin was prepared from 1 g of 2,4-dimethoxybenzhydrylamine resin, 214 mg of Fmoc-Gly-OH, 110 mg of HOBt and 0.12 ml of DIC by the steps 1–5 in the coupling process.

Then the protecting group was removed by the steps 6–10 in the N$^\alpha$-deprotection process to obtain H-Gly-resin.

The coupling and N$^\alpha$-deprotection processes were repeated in the same manner to prepare H-Asn-Cys(Trt)-Sar-Arg(Mtr)-Gly-resin, followed by another coupling process using pGlu-OH to obtain pGlu-Asn-Cys(Trt)-Sar-Arg(Mtr)-Gly-resin. After drying, the resin was stirred in TFA-anisole-thiophenol (10-1-1 ml) for 4 hours, filtered and washed with TFA.

After the TFA solution was placed for 2 hours at room temperature, TFA was distilled off. To the residue, a mixture of ether and water was added. Aqueous portion was collected and freeze-dried.

The obtained freeze-dried peptide was dissolved in 10 ml of 0.05 % aqueous TFA solution. 40 rag of cystine S-monoxide was added to the solution under chilling with ice, and the resulting mixture was stirred for 30 minutes.

Then the resulting solution was purified by high-performance liquid chromatography at 12 ml/min. (flow rate), 0 to 10 % (B) 20 min. linear gradient (A) (mobile phase), subjected to Dowex 1×2 (acetate type) treatment and freeze-dried to obtain the desired compound.

Yield: 98 rag
R$_f^3$ : 0.10
$[\alpha]_D$ : −137.8° (c=0.5, water )
FAB mass spectrum (M+1) : 749

EXAMPLE 2

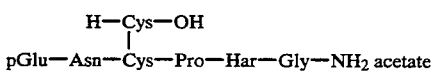

pGlu—Asn—Cys—Pro—Har—Gly—NH$_2$ acetate pGlu-Asn-Cys(Trt)-Pro-Har(Mtr)-Gly-resin was prepared from 1 g of 2,4-dimethoxybenzhydrylamine resin in the same manner as in Example 1. After TFA treatment, the resulting resin was reacted with cystine S-monoxide in the same manner as in Example 1.

Then the purification was carried out by high-performance liquid chromatography, and ion exchange treatment was performed in the same manner as in Example 1, followed by freeze-drying to obtain the desired compound.

Yield: 108 mg
R$_f^3$ : 0.10
$[\alpha]_D$ : −161.6° (c=0.5, water)
FAB mass spectrum (M+1) : 789

EXAMPLE 3

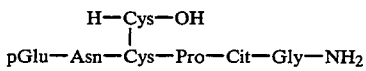

pGlu—Asn—Cys—Pro—Cit—Gly—NH$_2$ pGlu-Asn-Cys(Trt)-Pro-Cit-Gly-resin was prepared from 1 g of 2,4-dimethoxybenzhydrylamine resin in the same manner as in Example 1. After TFA treatment, the resulting resin was reacted with cystine S-monoxide in the same manner as in Example 1.

Then the purification was carried out by high-performance liquid chromatography, and ion exchange treatment was performed in the same manner as in Example 1, followed by freeze-drying to obtain the desired compound.

Yield: 92 mg
R$_f^3$ : 0.12
$[\alpha]_D$ : −165.6° (c=0.5, water)
FAB mass spectrum (M+1) : 776

EXAMPLE 4

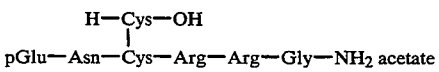

pGlu—Asn—Cys—Arg—Arg—Gly—NH$_2$ acetate pGlu-Asn-Cys(Trt)-Arg(Mtr)-Arg(Mtr)-Gly-resin was prepared from 1 g of 2,4-dimethoxybenzhydrylamine resin in the same manner as in Example 1. After TFA treatment, the resulting resin was reacted with cystine S-monoxide in the same manner as in Example.

Then the purification was carried out by high-performance liquid chromatography, and ion exchange treatment was performed in the same manner as in Example 1, followed by freeze-drying to obtain the desired compound.

Yield: 99 mg
R$_f^3$ : 0.06
$[\alpha]_D$ : −108.8° (c=0.5, water)
FAB mass spectrum (M+1) : 834

EXAMPLE 5

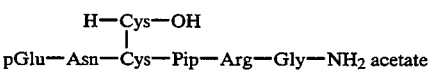

pGlu—Asn—Cys—Pip—Arg—Gly—NH$_2$ acetate pGlu-Asn-Cys(Trt)-Pip-Arg(Mtr)-Gly-resin was prepared from 1 g of 2,4-dimethoxybenzhydrylamine resin in the same manner as in Example 1. After TFA treatment, the resulting resin was reacted with cystine S-monoxide in the same manner as in Example 1.

Then the purification was carried out by high-performance liquid chromatography, and ion exchange treatment was performed in the same manner as in Example 1, followed by freeze-drying to obtain the desired compound.

Yield: 55 mg
R$_f^3$ : 0.09
$[\alpha]_D$ : −134.4° (c=0.5, water)
FAB mass spectrum (M+1) : 7 89

EXAMPLE 6

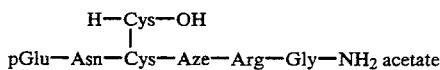
pGlu—Asn—Cys—Aze—Arg—Gly—NH₂ acetate pGlu-Asn-Cys(Trt)-Aze-ArG(Mtr)-Gly-resin was prepared from 1 g of 2,4-dimethoxybenzhydrylamine resin in the same manner as in Example 1. After TFA treatment, the resulting resin was reacted with cystine S-monoxide in the same manner as in Example 1.

Then the purification was carried out by high-performance liquid chromatography, and ion exchange treatment was performed in the same manner as in Example 1, followed by freeze-drying to obtain the desired compound.
Yield: 98 mg
$R_f^3$ : 0.08
$[\alpha]_D$ : −159.0° (c=0.5, water)
FAB mass spectrum (M+1) : 761

EXAMPLE 7

H-Asn-Ser-Pro-Arg-OH acetate (1) Boc-Pro-ArG(NO₂)-OBzl
To a solution of 15 g of H-Arg(NO₂)-OBzl in 250 ml of THF, 15 G of Boc-Pro-OSu was added under chilling with ice, followed by stirring for 18 hours at room temperature.

After THF was distilled off, the residue was dissolved in AcOEt. The AcOEt solution was washed successively with dilute HCl saturated aqueous NaHCO₃ solution and water, followed by drying over anhydrous Na₂SO₄.

AcOEt was distilled off. The residue was dissolved in CHCl₃-MeOH, and purified by silica-gel column chromatography to obtain the desired compound as an oily product.
Yield: 22 g
$R_f^1$ 0.61, $R_f^2$ : 0.77
$[\alpha]_D$ : 37.1° (c=1.0, DMF)

(2) Boc-Ser(Bzl)-Pro-Arg(NO₂)-OBzl
22 g of Boc-Pro-Arg(NO₂)-OBzl was placed in 110 ml of 4 N HCl-AcOEt for 30 min. at room temperature, and then the solvent was distilled off.

After drying under reduced pressure, the residue was dissolved in 150 ml of DMF. To the solution, 9 ml of Et₃N, 12.8 g of Boc-Ser(Bzl)-OH, 10 g of HOBt and 9.4 g of DCC were added under chilling with ice, followed by stirring for 18 hours at room temperature.

DCUrea was removed by filtration, and DMF was distilled off. The residue was dissolved in AcOEt. Then the AcOEt solution was washed successively with dilute HCl, saturated aqueous NaHCO₃ solution and water, followed by drying over anhydrous Na₂SO₄.

AcOEt was distilled off, and the residue was treated with AcOEt-ether to give the desired compound as a crystalline product.
Yield: 21 Q
M.P. 80°-82° C.
$R_f^1$ : 0.67, $R_f^2$ : 0.83
$[\alpha]_D$ −30.8° (c=1.0, DMF)

(3) Z-Asn-Ser (Bzl) - Pro-Arg (NO₂) -OBzl
4.0 9 of Boc-Ser(Bzl)-Pro-Arg(NO₂)-OBzl was placed in 15 ml of 4 N HCl-AcOEt for 30 min. at room temperature, and the solvent was distilled off.

To the residue, 2-butanol - CH₂Cl₂ (5:1 v/v) and saturated aqueous NaHCO3 solution was added. The organic portion was collected and washed with saturated aqueous NaCl solution, followed by drying over anhydrous Na₂SO₄.

The solvent was distilled off, and the residue was dissolved in 50 ml of DMF. To the solution, 1.55 g of Z-Asn-OH, 1.3 g of HOBt and 1.3 g of DCC were added under chilling with ice.

After stirring for 18 hours at room temperature, DCUrea was removed by filtration, and DMF was distilled off.

The residue was dissolved in 2-butanol - CH₂Cl₂ (5:1 v/v). Then the solution was washed successively with saturated aqueous NaHCO₃ solution, dilute HCl saturated with NaCl and saturated aqueous NaCl solution, followed by drying over anhydrous Na₂SO₄.

The solvent was distilled off, and the residue was treated with ether to give the desired compound as a crystalline product.
Yield: 4.5 g
M.P. : 205°-209° C. (decomposed)
$R_f^1$ : 0.55, $R_f^2$ : 0.72
$[\alpha]_D$ : −25.1° (c=1.0, DMF) (4) H-Asn-Ser-Pro-Arg-OH acetate A solution of 150 mg of Z-Asn-Ser(Bzl)-Pro-Arg(NO₂)-OBzl in 20 ml of 80 % acetic acid was stirred for 18 hours in a stream of hydrogen gas in the presence of 10 % palladium-carbon.

The palladium-carbon was removed by filtration, and the solvent was distilled off. The residue was dissolved in water, then freeze-dried.

Then the resulting product was purified by high-performance liquid chromatography at 12 ml/min.(flow rate), 0 to 10 % (B) 20 min. linear gradient (A) (mobile phase), subjected to Dowex 1×2 (acetate type) treatment and freeze-dried to obtain the desired compound.
Yield: 82 mg
$R_f^3$ : 0.15
$[\alpha]_D$ : −70.4° (c=0.5, water)
FAB mass spectrum (M+1) : 473

EXAMPLE 8

H-Asn-Thr-Pro-Arg-OH acetate (1) Boc-Thr-Pro-Arg (NO₂)-OBzl
9.6 g of Boc-Pro-Arg(NO₂)-OBzl was placed in 50 ml of 4 N HCl-AcOEt for 30 min. at room temperature, and the solvent was distilled off.

After drying under reduced pressure, the residue was dissolved in 100 ml of DMF. To the solution, 4 ml of Et₃N and 6 g of Boc-Thr-OSu were added under chilling with ice, followed by stirring for 18 hours at room temperature.

DMF was distilled off and the residue was dissolved in AcOEt. Then the AcOEt solution was washed successively with saturated aqueous NaHCO₃ solution, dilute HCl and water, followed by drying over anhydrous Na₂SO₄.

AcOEt was distilled off, and the residue was purified with CHCl₃-acetone by silica-gel column chromatography, then was treated with ether to give the desired compound as a crystalline product.
Yield: 7.1 g
M.P. : 86°-91° C.
$R_f^1$ : 0.59, $R_f^2$ : 0.77
$[\alpha]_D$ : −37.5° (c=1.0, DMF)

(2) Z-Asn-Thr-Pro-Arg (NO₂) -OBzl
The desired compound was prepared from 3.0 g of Boc-Thr-Pro-Arg(NO₂)-OBzl, 15 ml of 4 N HCl- AcOEt, 1.2 g Z-Ash-OH, 1.2 g of HOBt and 1.1 g of DCC in the same manner as in Example 7-(3).
Yield: 2.4 l
M.P. 184°–186° C.
$R_f^1$: 0.39, $R_f^2$: 0.62
$[\alpha]_D$: −30.2° (c=1.0, DMF)

(3) H-Asn-Thr-Pro-Arg-OH acetate 150 mg of Z-Asn-Thr-Pro-Arg(NO$_2$)-OBzl was reduced in the presence of palladium-carbon in the same manner as in Example 7-(4). The resulting product was purified by high-performance liquid chromatography at 12 ml/min. (flow rate), to 10 % (B) 20 min. linear gradient (A) (mobile phase), subjected to Dowex 1×2 (acetate type) treatment and freeze-dried to obtain the desired compound.
Yield: 104 mg
$R_f^3$: 0.17
$[\alpha]_D$: −58.5° (c=0.5, water)
FAB mass spectrum (M+1): 487

EXAMPLE 9

H-Asn-Ala-Pro-Arg-OH acetate (1) Boc-Ala-Pro-Arg (NO$_2$)-OBzl

The desired compound was prepared from 28.9 g of Boc-Pro-Arg (NO$_2$)-OBzl, 150 ml of 4 N HCl-AcOEt, 8 ml of Et$_3$N and 16.3 g of Boc-Ala-OSu in the same manner as in Example 8-(1).
Yield: 25.0 g
M.P.: 83°–85° C.
$R_f^1$: 0.61, $R_f^2$: 0.77 $[\alpha]_D$: −54.2° (c=1.0, DMF)

(2) Z-Asn-Ala-Pro-Arg(NO$_2$)-OBzl

The desired compound was prepared from 2.9 g of Boc-Ala-Pro-Arg(NO$_2$)-OBzl, 15 ml of 4 N HCl-AcOEt, 1.4 g of Z-Asn-OH, 1.0 g of HOBt and 1.1 g of DCC in the same manner as in Example 7-(3).
Yield: 2.8 g
M.P. 128°–130° C.
$R_f^1$: 0.45, $R_f^2$: 0.65
$[\alpha]_D$: −36.8° (c=1.0, DMF)

(3) H-Asn-Ala-Pro-Arg-OH acetate 150 mg of Z-Asn-Ala-Pro-Arg(NO$_2$)-OBzl was reduced in the presence of palladium-carbon in the same manner as in Example 7-(4). The resulting product was purified by high-performance liquid chromatography at 12 ml/min. (flow rate), 0 to 10% (B) 20 rain, linear gradient (A) (mobile phase), subjected to Dowex 1×2 (acetate type) treatment and freeze-dried to obtain the desired compound.
Yield: 100 mg
$R_f^3$: 0.14
$[\alpha]_D$: −78.5° (c=0.5, water)
FAB mass spectrum (M+1): 457

EXAMPLE 10

H-Asn-Ser-D-Pro-Arg-OH acetate (1) Boc-D-Pro-Arg (NO$_2$)-OBzl

The desired compound was prepared as an oily product from 9 g of H-Arg(NO$_2$)-OBzl and 9 g of Boc-D-Pro-OSu in the same manner as in Example 7-(1).
Yield: 13 g
$R_f^1$: 0.64, $R_f^2$: 0.76
$[\alpha]_D$ +9.6° (c=1.9, DMF)

(2) Boc-Ser(Bzl)-D-Pro-Arg(NO$_2$)-OBzl

The desired compound was prepared as an oily product from 12 g of Boc-D-Pro-Arg(NO$_2$)-OBzl, 60 ml of 4 N HCl-AcOEt, 3.3 ml of Et$_3$N, 7 g of Boc-Ser(Bzl)-OH, 4.2 g of HOBt and 5.1 g of DCC in the same manner as in Example 7-(2).
Yield: 10 g
$R_f^1$: 0.71, $R_f^2$: 0.80
$[\alpha]_D$: +7.4° (c=1.0, DMF)

(3) Z-Asn-Ser(Bzl)-D-Pro-Arg (NO$_2$)-OBzl

The desired compound was prepared from 3.0 g of Boc-Ser(Bzl)-D-Pro-Arg(NO$_2$)-OBzl, 10 ml of 4 N HCl-AcOEt, 1.2 g of Z-Ash-OH, 0.9 g of HOBt and 0.95 g of DCC in the same manner as in Example 7-(3).
Yield: 2.5 g
M.P. 89°–92° C.
$R_f^1$: 0.59, $R_f^2$: 0.72 $[\alpha]_D$ +14.8° (c=1.0, DMF)

(4) H-Asn-Ser-D-Pro-Arg-OH acetate 100 mg of Z-Asn-Ser(Bzl)-D-Pro-Arg(NO$_2$)-OBzl was reduced in the presence of palladium-carbon in the same manner as in Example 7-(4). The resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.
Yield: 48 mg
$R_f^3$: 0.13
$[\alpha]_D$: +25.3° (c=0.5, water)
FAB mass spectrum (M+1): 473

EXAMPLE 11

H-Asn-Ser-Pro-Arg-Gly-NH$_2$ acetate

Fmoc-Gly-resin was prepared from 1 g of 2,4-dimethoxybenzhydrylamine resin, 214 mg of Fmoc-Gly-OH, 110 mg of HOBt and 0.12 ml of DIC by the above described coupling process.

Then the protecting group was removed by N$^\alpha$-deprotection process to obtain H-Gly-resin.

The coupling and N$^\alpha$-deprotection processes were repeated in the same manner to prepare H-Asn-Ser (Bu$^t$)-Pro-Arg(Mtr)-Gly-resin. After drying, the resin was stirred in TFA-anisole (10-1 ml) for 4 hours at room temperature. The resin was removed by filtration and was washed with TFA.

After the TFA solution was placed for 2 hours at room temperature, TFA was distilled off. To the residue, ether-water was added, and the aqueous portion was collected and was subjected to Dowex 1×2 (acetate type) treatment and freeze-dried.

Then the resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.
Yield: 56 mg
$R_f^3$: 0.11
$[\alpha]_D$: −78.8° (c=0.5, water)
FAB mass spectrum (M+1): 529

EXAMPLE 12

H-Asn-Ser-Pip-Arg-OH acetate (1) Boc-Pip-Arg(NO$_2$)-OBzl

To a solution of 10.6 g of H-Arg(NO$_2$)-OBzl in 100 ml of DMF, 7.1 g of Boc-Pip-OH, 7.1 g of HOBt and 6.7 g of DCC were added under chilling with ice. The mixture was stirred for 18 hours at room temperature. The produced DCUrea was removed by filtration, and DMF was distilled off.

The residue was dissolved in AcOEt. The resulting solution was washed successively with saturated aqueous NaHCO$_3$ solution, dilute HCl and water, followed by drying over anhydrous Na$_2$SO$_4$.

AcOEt was distilled off, and the residue was purified with CHCl$_3$-acetone by silica-gel column chromatography to obtain the desired compound as an oily product.

Yield: 5.5 g
R$_f^1$ : 0.68, R$_f^2$ : 0.80
$[\alpha]_D$ : −24.0° (c=1.0, DMF)

(2) Boc-Ser(Bzl)-Pip-Arg(NO$_2$)-OBzl 5.2 g of Boc-Pip-Arg(NO$_2$)-OBzl was placed in 25 ml of 4 N HCl-AcOEt for 30 min. at room temperature, and then the solvent was distilled off.

The residue was dried under reduced pressure and then dissolved in 50 ml of DMF. To the resulting solution, 1.4 ml of Et$_3$N and 3.9 g of Boc-Ser(Bzl)-OSu were added under chilling with ice, and then stirred for 18 hours at room temperature.

DMF was distilled off and the residue was dissolved in AcOEt. The resulting solution was washed successively with H saturated aqueous NaHCO$_3$ solution, dilute HCl and water, followed by drying over anhydrous Na$_2$SO$_4$.

AcOEt was distilled off, and the residue was purified with CHCl$_3$-acetone by silica-gel column chromatography to obtain the desired compound as an oily product.

Yield: 2.8 g
R$_f^1$ : 0.74, R$_f^2$ : 0.86
$[\alpha]_D$ : −42.6° (c=1.0, DMF)

(3) Boc-Asn-Ser(Bzl)-Pip-Arg(NO$_2$)-OBzl 1.6 g of Boc-Ser(Bzl)-Pip-Arg(NO$_2$)-OBzl was placed in 6 ml of 4 N HCl-AcOEt for 30 min. at room temperature, and then the solvent was distilled off.

To the residue, 2-butanol CH$_2$Cl$_2$ (5:1 v/v) and saturated aqueous NaHCO$_3$ solution were added. The organic portion was collected and then the solution was washed with saturated aqueous NaCl solution, followed by drying over anhydrous Na$_2$SO$_4$.

The solvent was distilled off, and then the residue was dissolved in 20 ml of DMF. To the resulting solution, 0.53 g of Boc-Asn-OH, 0.53 g of HOBt and 0.52 g of DCC were added under chilling with ice.

The resulting solution was stirred for 18 hours at room temperature, and then DCUrea was removed by filtration and DMF was distilled off.

The residue was dissolved in AcOEt, and the solution was washed successively with saturated aqueous NaHCO$_3$ solution, dilute HCl and saturated aqueous NaCl solution, followed by drying over anhydrous Na$_2$SO$_4$.

The solvent was distilled off, and the residue was purified with CHCl$_3$-MeOH by silica-gel column chromatography to obtain the desired compound as an oily product.

Yield: 1.0 g
R$_f^1$ : 0.57, R$_f^2$ : 0.74
$[\alpha]_D$ : −37.8° (c=1.0, DMF)

(4) H-Asn-Ser-Pip-Arg-OH acetate 150 mg of Boc-Asn-Ser(Bzl)-Pip-Arg(NO$_2$)-OBzl was placed in 0.5 ml of 4 N HCl-AcOEt for 30 min. at room temperature, and then the solvent was distilled off.

To the residue, 20 ml of 80% acetic acid was added and then the resulting mixture was stirred for 18 hours in a stream of hydrogen gas in the presence of 10% palladium-carbon.

The palladium-carbon was removed by filtration, and the solvent was distilled off. The residue was dissolved in water, and then freeze-dried.

Then the resulting product was purified by high-performance liquid chromatography at 12 ml/min.(flow rate), 0 to 10% (B) 20 min. linear gradient (A) (mobile phase), subjected to Dowex 1×2 (acetate type) treatment and freeze-dried to obtain the desired compound.

Yield: 63 mg
R$_f^3$ : 0.19
$[\alpha]_D$ : −46.2° (c=0.5, water)
FAB mass spectrum (M+1) : 487

EXAMPLE 13

H-Pro-Ser-Pip-Arg-OH acetate (1) Z-Pro-Set (Bzl) -Pip-Arg (NO$_2$)-OBzl

The desired compound was prepared as an oily product from 1.0 g of Boc-Ser(Bzl)-Pip-ArG(NO$_2$)-OBzl, 5 ml of 4 N HCl-AcOEt, 0.2 ml of Et$_3$N and 0.49 g of Z-Pro-OSu in the same manner as in Example 12- (1 ).

Yield: 0.9 g
R$_f^1$ : 0.72, R$_f^2$ : 0.82
$[\alpha]_D$ : −51.2° (c=1.0, DMF)

(2) H-Pro-Ser-Pip-Arg-OH acetate 150 mg of Z-Pro-Ser(Bzl)-Pip-ArG(NO$_2$)-OBzl was reduced in the presence of palladium-carbon in the same manner as in Example 12-(4). The resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 31 mg
R$_f^3$ : 0.18
$[\alpha]_D$ : −76.5° (c=0.5, water)
FAB mass spectrum (M+1) : 470

EXAMPLE 14

H-Pro-Asn-Set-Pip-Arg-OH acetate (1) Z-Pro-Asn-Ser(Bzl)-Pip-Arg(NO$_2$)-OBzl

The desired compound was prepared from 0.68 g of Boc-Asn-Ser(Bzl)-Pip-ArG(NO$_2$)-OBzl, 3 ml of 4 N HCl-AcOEt, 0.14 ml of NMM and 0.32 g of Z-Pro-OSu in the same manner as in Example 12-(2) .

Yield: 0.7 g
M.P. 95°–97° C.
R$_f^1$ : 0.57, R$_f^2$ : 0.74
$[\alpha]_D$ −48.2° (c=1.0, DMF)

(2) H-Pro-Asn-Ser-Pip-Arg-OH acetate 150 mg of Z-Pro-Asn-Ser(Bzl)-Pip-Arg(NO$_2$)-OBzl was reduced in the presence of palladium-carbon in the same manner as in Example 12-(4). The resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 60 mg
R$_f^3$ : 0.14
$[\alpha]_D$ : −76.4° (c=0.5, water )
FAB mass spectrum (M+1) : 584

EXAMPLE 15

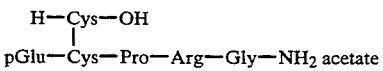

pGlu—Cys—Pro—Arg—Gly—NH$_2$ acetate (1) Z-Arg(Mbs)-Gly-NH$_2$

In a mixture of 100 ml of AcOEt and 70 ml of 5% aqueous citric acid was dissolved under stirring 10 g of Z-Arg(Mbs)-OH dicyclohexylamine salt. The AcOEt portion was washed with water and dried over anhydrous Na$_2$SO$_4$.

The solvent was distilled off. The residue was dissolved in 100 ml of DMF. To the DMF solution were added under chilling with ice 1.7 g of H-Gly-NH$_2$ hydrochloride, 1.7 ml of NMM, 2 g of HOBt and 3.4 g of DCC. The mixture was stirred for 18 hours at room temperature. The produced DCUrea was removed by filtration, and DMF was distilled off.

The residue was dissolved in a mixture of 2-butanol and CH$_2$Cl$_2$ (5:1, v/v). The resulting solution was washed successively with saturated aqueous NaHCO$_3$ solution, dilute HCl saturated with NaCl and saturated aqueous NaCl solution, and then dried over anhydrous Na$_2$SO$_4$.

The solvent was distilled off. The residue was treated with MeOH-ether to give the desired compound as a crystalline product.

Yield: 5.0 g
M.P. : 201°–202° C.
R$_f^1$ 0.26 Rf$^2$ 0.55
$[\alpha]_D$ +2.1° (c=0.5, DMF)

(2) BoC-Pro-ArG(Mbs)-Gly-NH$_2$

A solution of 20.8 g of Z-Arg(Mbs)-Gly-NH$_2$ in 200 ml of 80% AcOH was stirred for 6 hours in a stream of hydrogen in the presence of 10% palladium-carbon.

The palladium-carbon was then removed by filtration and the solvent was distilled off from the filtrate. The residue was dried under reduced pressure and then dissolved in 200 ml of DMF. To the resulting solution were added 4.3 ml of NMM and 12.1 g of Boc-Pro-OSu, and the mixture was stirred for 18 hours at room temperature.

DMF was distilled off. The residue was dissolved in a mixture of 2-butanol and CH$_2$Cl$_2$ (5:1, v/v). The resulting solution was washed successively with saturated aqueous NaHCO$_3$ solution, dilute HCl saturated with NaCl and saturated aqueous NaCl solution, and then dried over anhydrous Na$_2$SO$_4$.

The solvent was distilled off. The residue was treated with ether to give the desired compound as a crystalline product.

Yield: 21.5 g
M.P. : 120°–126° C.
R$_f^1$ : 0.31 R$_f^2$ : 0.53
$[\alpha]_D$ −26.5° (c=1, DMF)

(3) Boc-Cys(Acm)-Pro-Arg(Mbs)-Gly-NH$_2$ 9.8 g of Boc-Pro-Arg(Mbs)-Gly-NH$_2$ was placed in a mixture of 100 ml of THF and 100 ml of 4 N HCl-AcOEt for 30 min. at room temperature, and then the solvent was distilled off.

The residue was dried under reduced pressure and then dissolved in 100 ml of DMF. To the DMF solution were added under chilling with ice 3.6 ml of NMM, 5.2 g of Boc-Cys(Acm)-OH, 2.7 g of HOBt and 3.7 g of DCC. The mixture was stirred for 18 hours at room temperature.

The DCUrea was removed by filtration, and DMF was distilled off. The residue was dissolved in a mixture of 2-butanol and CH$_2$Cl$_2$ (5:1, v/v). The resulting solution was washed successively with saturated aqueous NaHCO$_3$ solution, dilute HCl saturated with NaCl and saturated aqueous NaCl solution, and then dried over anhydrous Na$_2$SO$_4$.

The solvent was distilled off. The residue was treated with ether to give the desired compound as a crystalline product.

Yield: 10.0 g
M.P. 110°–116° C.
R$_f^1$ : 0.24, R$_f^2$ : 0.50
$[\alpha]_D$ : 58.2° (c=0.5, DMF)

(4) Z-pGlu-Cys(Acm)-Pro-Arg(Mbs)-Gly-NH$_2$ 1.6 g of Boc-Cys(Acm)-Pro-Arg(Mbs)-Gly-NH$_2$ was placed in 10 ml of 4 N HCl-AcOEt for 30 min. at room temperature, and then the solvent was distilled off.

The residue was dried under reduced pressure and then dissolved in 20 ml of DMF. To the mixture were added under chilling with ice 0.22 ml of NMM and 0.86 g of Z-pGlu-OSu. The mixture was stirred for 18 hours at room temperature.

DMF was distilled off. The residue was dissolved in a mixture of 2-butanol and CH$_2$Cl$_2$ (5:1, v/v). The resulting solution was washed successively with saturated NaHCO$_3$ aqueous solution, dilute HCl saturated with NaCl and saturated NaCl aqueous solution, and then dried over anhydrous Na$_2$SO$_4$.

The solvent was distilled off. The residue was treated with ether to give the desired compound as a crystalline product.

Yield: 1.4 g
M.P. 95°–99° C.
R$_f^1$ : 0.11, F$_f^2$ : 0.40
$[\alpha]_D$ −44.7° (c=1.0, DMF)

(5) Z-pGlu-Cys(Scm)-Pro-Arg(Mbs)-Gly-NH$_2$

To a solution of 1.3 g of Z-pGlu-Cys (Acm)-Pro-Arg(Mbs)-Gly-NH$_2$ in 80 ml of CH$_2$Cl$_2$-MeOH (1:1, v/v) was added under chilling with ice 0.22 ml of Cl-Scm. The resulting mixture was stirred for 20 min.

The solvent was distilled off. The residue was purified with CHCl$_3$-MeOH by silica-gel column chromatography to obtain the desired compound as a crystalline product.

Yield: 540 mg
M.P. : 185°–190° C.
R$_f^1$ : 0.19, R$_f^2$ : 0.49
$[\alpha]_D$ : −64.0° (c=1.0, DMF)

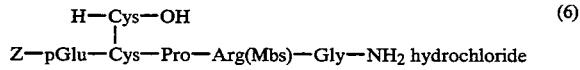

(6)

To a solution of 500 mg of Z-pGlu-Cys(Scm)-Pro-Arg(Mbs)-Gly-NH$_2$ in 10 ml of DMF was added 210 mg of cysteine hydrochloride and the mixture was stirred for 1 hour at room temperature.

The solvent was distilled off. The residue was purified with CHCl$_3$-MeOH by silica-gel column chromatography and was treated with ether to obtain the desired compound as a crystalline product.

Yield: 400 mg
M.P. : 145°–151° C. (decomposed)
R$_f^2$ : 0.12
$[\alpha]_D$ : −87.0° (c=1.0, DMF )

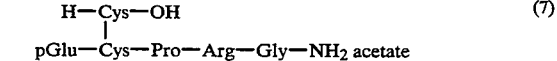

(7)

150 mg of Z-pGlu-Cys-Pro-Arg (Mbs)-Gly-NH$_2$

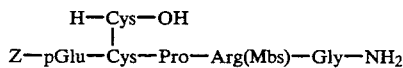

hydrochloride was placed in a mixture of 2 ml of MSA and 0.2 ml of anisole and the resulting mixture was stirred for 1 hour at room temperature. After addition of ether, the supernatant portion was removed.

The precipitate was dissolved in water. The solution was subjected to Dowex 1×2 (acetate type) treatment and water was distilled off.

The residue was dissolved in 0.05% TFA and purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 40 mg
$R_f^3$ : 0.11
$[\alpha]_D$ : 160.4° (c=0.5, water)
FAB mass spectrum (M+1) : 661

EXAMPLE 16

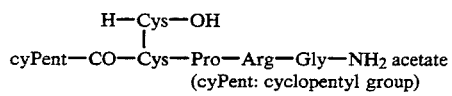
(cyPent: cyclopentyl group)

(1) cyPent-CO-Cys(Acm)-Pro-Arg(Mbs)-Gly-NH$_2$ 1.5 g of Boc-Cys(Acm)-pro-Arg(Mbs)-Gly-NH$_2$ was placed in 10 ml of 4 N HCl-AcOEt for 30 min. at room temperature and the solvent was distilled off.

The residue was dried under reduced pressure and dissolved in 15 ml of DMF. To the solution were added under chilling with ice 0.32 ml of NMM and anhydrous cyclopentane carboxylic acid (prepared from 0.48 g of cyclopentane carboxylic acid and 0.43 g of DCC) in 2 ml of DMF. The mixture was stirred for 4 hours at room temperature and DMF was distilled off.

The residue was dissolved in 2-butanol-CH$_2$Cl$_2$ (5:1 v/v). The resulting solution was washed successively with saturated aqueous NaHCO$_3$ solution, dilute HCl saturated with NaCl and saturated aqueous NaCl solution, and then dried over anhydrous Na$_2$SO$_4$.

The solvent was distilled off. The residue was purified with CHCl$_3$-MeOH by silica-gel column chromatography and was treated with ether to obtain the desired compound as a crystalline product.

Yield: 750 mg
M.P. : 135°–138° C.
$R_f^1$ : 0.16, $R_f^2$ : 0.45
$[\alpha]_D$ : −54.7° (C=1.0, DMF)

(2) cyPent-CO-Cys(Scm)-Pro-Arg(Mbs)-Gly-NH$_2$

The desired compound was prepared from 700 mg of cyPent-CO-Cys(Acm)-Pro-Arg(Mbs)-Gly-NH$_2$ and 0.14 ml of Cl-Scm in the same manner as in Example 15-(5).

Yield: 640 mg
M.P. : 130°–133° C.
$R_f^1$ : 0.28, $R_f^2$ : 0.55
$[\alpha]_D$ : −65.2° (C=1.0, DMF)

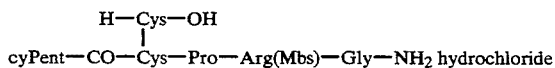
(3)

The desired compound was prepared from 600 mg of cyPent-CO-CYs(Scm)-Pro-Arg(Mbs)-Gly-NH$_2$ and 335 mg of cysteine hydrochloride in the same manner as in Example 15-(6).

Yield: 686 mg
M.P. : 142°–145° C.
$R_f^2$ : 0.18
$[\alpha]_D$ : −77.8° (c=1.0, DMF)

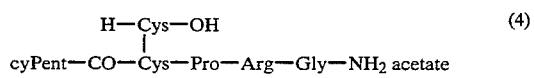
(4)

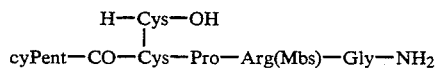

hydrochloride was treated with MSA-anisole in the same manner as in Example 15-(7), purified by high-performance liquid chromatography at 12 ml/min. (flow rate), 5 to 25% (B) 20 min. linear gradient (A) (mobile phase), subjected to Dowex 1×2 (acetate type) treatment and freeze-dried to obtain the desired compound.

Yield: 29 mg
$R_f^3$ : 0.32
$[\alpha]_D$ : −167.2° (c=0.5, water)
FAB mass spectrum (M+1) : 646

EXAMPLE 17

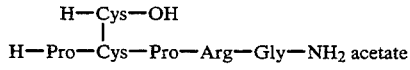

(1) Boc-Pro-Cys(Acm)-pro-Arg(Mbs)-Gly-NH$_2$ 1.5 g of Boc-Cys(Acm)-Pro-Arg(Mbs)-Gly-NH$_2$ was placed in 10 ml of 4 N HCl-AcOEt for 30 min. at room temperature and the solvent was distilled off.

The residue was dried under reduced pressure and dissolved in 20 ml of DMF. To the solution were added under chilling with ice 0.32 ml of NMM and 0.67 g of Boc-Pro-OSu. After the mixture was stirred for 18 hours at room temperature, and DMF was distilled off.

The residue was dissolved in 2-butanol-CH$_2$Cl$_2$ (5:1 v/v). The resulting solution was washed successively with saturated aqueous NaHCO$_3$ solution, dilute HCl saturated with NaCl and saturated aqueous NaCl solution, and then dried over anhydrous Na$_2$SO$_4$.

The solvent was distilled off. The residue was purified with CHCl$_3$-MeOH by silica-gel column chromatography and treated with ether to obtain the desired compound as a crystalline product.

Yield: 0.6 g
M.P. : 165°–168° C.
$R_f^1$ : 0.20, $R_f^2$ : 0.49
$[\alpha]_D$ : −83.0° (c=1.0, DMF)

(2) Boc-Pro-Cys(Scm)-Pro-Arg(Mbs)-Gly-NH$_2$

The desired compound was prepared from 450 mg of Boc-Pro-Cys(Acm)-Pro-Arg(Mbs)-Gly-NH$_2$ and 0.08 ml of Cl-Scm in the same manner as in Example 15-(5)

Yield: 435 mg
M.P. : 205°–210° C.
$R_f^1$ : 0.33, $R_f^2$ : 0.57
$[\alpha]_D$ : −78.4° (c=1.0, DMF)

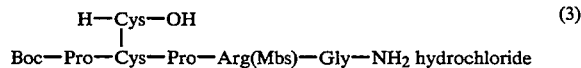
(3)
Boc—Pro—Cys—Pro—Arg(Mbs)—Gly—NH₂ hydrochloride

The desired compound was prepared from 400 mg of Boc-Pro-Cys(Scm)-Pro-Arg(Mbs)-Gly-NH₂ and 197 mg of cysteine hydrochloride in the same manner as in Example 15-(6).
Yield: 416 mg
M.P. : 172°–180° C. (decomposed)
$R_f{}^2$ : 0.23
$[\alpha]_D$ : −82.1° (c=1.0, DMF)

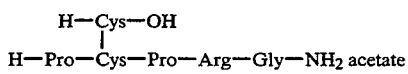
(4)
H—Pro—Cys—Pro—Arg—Gly—NH₂ acetate

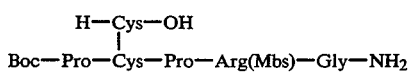
Boc—Pro—Cys—Pro—Arg(Mbs)—Gly—NH₂ hydrochloride was treated with MSA-anisole in the same manner as in Example 15-(7), purified by high-performance liquid chromatography at 12 ml/min. (flow rate), 0 to 10 (B) 20 min. linear gradient (A) (mobile phase), subjected to Dowex 1×2 (acetate type) treatment and freeze-dried to obtain the desired compound.
Yield: 22 mg
$R_f{}^3$ : 0.06
$[\alpha]_D$ : −140.6° (c=0.5, water)
FAB mass spectrum (M+1) : 647

EXAMPLE 18

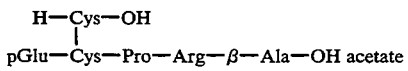
pGlu—Cys—Pro—Arg—β—Ala—OH acetate (1) Boc-Arg(Mbs)-β-Ala-OBzl

To a solution of 3.5 g of H-β-Ala-OBzl p-toluene-sulfonate in 50 ml of DMF were added under chilling with ice 1.4 ml of Et₃N, 3.0 g of Boc-Arg(Mbs)-OH, 1.3 g of HOBt and 1.5 g of DCC.

The mixture was stirred for 18 hours at room temperature, DCUrea was removed by filtration, and DMF was distilled off.

The residue was dissolved in AcOEt and the resulting solution was washed successively with saturated aqueous NaHCO₃ solution, dilute HCl and water, and then dried over anhydrous Na₂SO₄.

AcOEt was distilled off to give the desired compound as an oily product.
Yield: 3.8 g
$R_f{}^1$ : 0.55, $R_f{}^2$ : 0.76
$[\alpha]_D$ : −0.5° (c=1.0, DMF)

(2) Boc-Pro-Arg(Mbs)-β-Ala-OBzl 3.6 g of Boc-Arg(Mbs)-β-Ala-OBzl was placed in 15 ml of 4 N HCl-AcOEt for 30 min. at room temperature and the solvent was distilled off.

The residue was dried under reduced pressure and dissolved in 50 ml of DMF. To the solution were added under chilling with ice 1.0 ml of NMM and 2.0 g of Boc-Pro-OSu and the mixture was stirred for 18 hours at room temperature.

DMF was distilled off. The residue was dissolved in AcOEt and washed successively with saturated aqueous NaHCO₃ solution, dilute HCl and saturated aqueous NaCl solution, and then dried over anhydrous Na₂SO₄.

AcOEt was distilled off to give the desired compound as an oily product.
Yield: 3.6 g
$R_f{}^1$ : 0.58, $R_f{}^2$ : 0.75
$[\alpha]_D$ : −28.9° (c=1.0 DMF)

(3) Boc-Cys(Acm)-Pro-Arg(Mbs)-β-Ala-OBzl

The desired compound was prepared from 3.5 g of Boc-Pro-Arg(Mbs)-β-Ala-OBzl, 15 ml of 4 N HCl-AcOEt, 0.82 m NMM and Boc-Cys (Acre)-OH symmetric acid anhydride (prepared from 3.2 g of Boc-Cys (Acre)-OH and 1.1 g of DCC) in the same manner as in Example 16-(1).
Yield: 4.1 g
M.P. : 79°–83° C.
$R_f{}^1$ : 0.49, $R_f{}^2$ : 0.74
$[\alpha]_D$ : −27.8° (c=1.0, DMF)

(4) Z-PGlu-Cys(Acm)-Pro-Arg(Mbs)-β-Ala-OBzl

The desired compound was prepared as an oily product from 1.7 g of Boc-Cys(Acm)-Pro-Arg(Mbs)-β-Ala-OBzl, 10 ml of 4 N HCl-AcOEt, 0.3 ml of NMM and 0.83 g of Z-pGlu-OSu in the same manner as in Example 15-(4).
Yield: 1.8 g
$R_f{}^1$ : 0.43, $R_f{}^2$ : 0.67
$[\alpha]_D$ : −42.2° (c=1.0, DMF)

(5) Z-pGlu-CyS(Scm)-Pro-Arg(Mbs)-β-Ala-OBzl

The desired compound was prepared as an oily product from 1.9 g of Z-pGlu-Cys(Acm)-Pro-Arg(Mbs)-β-Ala-OBzl and 0.29 ml of Cl-Scm in the same manner as in Example 15-(5).
Yield: 1.2 g
$R_f{}^1$ : 0.47, $R_f{}^2$ : 0.73
$[\alpha]_D$ : −64.3° (C=1.0, DMF)

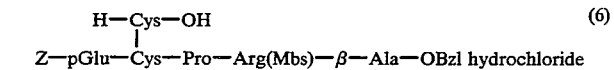
(6)
Z—pGlu—Cys—Pro—Arg(Mbs)—β—Ala—OBzl hydrochloride

The desired compound was prepared from 1.0 g of Z-pGlu-Cys(Scm)-Pro-Arg(Mbs)-β-Ala-OBzl and 0.4 g of cysteine hydrochloride in the same manner as in Example 15-(6).
Yield: 980 mg
M.P. : 133-20 137° C.
$R_f{}^2$ : 0.45
$[\alpha]_D$ : −71.9° (c=1.0, DMF)

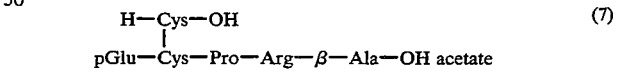
(7)
pGlu—Cys—Pro—Arg—β—Ala—OH acetate

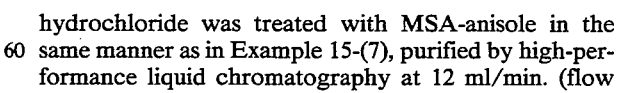
Z—pGlu—Cys—Pro—Arg(Mbs)—β—Ala—OBzl hydrochloride was treated with MSA-anisole in the same manner as in Example 15-(7), purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.
Yield: 27 mg
$R_f{}^3$ : 0.14
$[\alpha]_D$ : −154.0° (c=0.5, water)
FAB mass spectrum (M+1) : 67 6

EXAMPLE 19

H-Pro-CYs-Pro-Arg-Gly-NH₂ acetate (1) Z-Pro-Cys(MBzl)-Pro-Arg(Mbs)-Gly-NH₂

The desired compound was prepared from 2.4 g of Boc-Cys(MBzl)-Pro-Arg(Mbs)-Gly-NH₂ 10 ml of 4 N HCl-AcOEt, 0.6 ml of NMM and 1.3 g of Z-Pro-OSu in the same manner as in Example 15-(4).

Yield: 2.3 G
M.P.: 101°–104° C.
$R_f^1$: 0.41, $R_f^2$: 0.61
$[\alpha]_D$: −56.4° (c=1.0, DMF)

(2) H-Pro-CYs-Pro-Arg-Gly-NH₂ acetate 150 mg of Z-Pro-Cys(MBzl)-Pro-Arg(Mbs)-Gly-NH₂ was treated with MSA-anisole in the same manner as in Example 15-(7), purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 64 mg
$R_f^3$ (including 0.1% ethanediol): 0.12
$[\alpha]_D$: −92.7° (c=0.5, water)
FAB mass spectrum (M+1): 528

EXAMPLE 20

(H—Pro—Cys—Pro—Arg—Gly—NH₂)₂ acetate

Into 2 ml of water was dissolved 30 mg of H-Pro-Cys-Pro-ArG-Gly-NH₂ acetate. The resulting solution was adjusted to have pH 7 with dilute aqueous ammonium, stirred for 7 days at room temperature, and then made acidic by addition of acetic acid and freeze-dried.

Yield: 28 mg
$R_f^3$: 0.02
$[\alpha]_D$: −142.9° (c=0.5, water)
FAB mass spectrum (M+1): 1054

EXAMPLE 21 pGlu-Asn-Ser-Pro-Arg-Gly-NH₂ acetate

Fmoc-Gly-resin was prepared from 1 g of 2,4-dimethoxybenzhydrylamine resin, 214 mg of Fmoc-Gly-OH, 110 mg of HOBt and 0.12 ml of DIC by the above described coupling process.

Then the protecting group was removed by $N^{\alpha}$-deprotection process to obtain H-Gly-resin.

The coupling and $N^{\alpha}$-deprotection processes were repeated in the same manner to prepare H-Asn-Ser(Bu$^t$)-Pro-Arg(Mtr)-Gly-resin, and then the coupling process using pGlu-OH were performed to obtain pGlu-Asn-Ser(Bu$^t$)-Pro-Arg(Mtr)-Gly-resin. After drying, the resin was stirred in TFA-anisole (10-1 ml) for 4 hours at room temperature. The resin was removed by filtration and was washed with TFA.

After the TFA solution was placed for 2 hours at room temperature, TFA was distilled off. To the residue, ether-water was added, and the aqueous portion was collected, subjected to Dowex 1×2 (acetate type) treatment and freeze-dried.

Then the resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 69 mg
$R_f^3$: 0.14
$[\alpha]_D$: −91.8° (c=0.5, water)
FAB mass spectrum (M+1): 640

EXAMPLE 22 pGlu-Asn-Ser-D-Pro-Arg-Gly-NH₂ acetate pGlu-Asn-Ser(But)-D-Pro-Arg(Mtr)-Gly-resin was prepared from 1 g of 2,4-dimethoxybenzhydrylamine resin in the same manner as in Example 21, and then TFA treatment, purification by high-performance liquid chromatography, ion exchange treatment and freeze-drying were performed in the same manner as in Example 21 to obtain the desired compound.

Yield: 74 mg
$R_f^3$: 0.15
$[\alpha]_D$: −13.9° (c=0.5, water)
FAB mass spectrum (M+1): 640

EXAMPLE 23 pGlu-Asn-Ser-Pro-D-Arg-Gly-NH₂ acetate pGlu-Asn-Ser(But)-Pro-D-Arg(Mtr)-Gly-resin was prepared from 1 g of 2,4-dimethoxybenzhydrylamine resin in the same manner as in Example 21, and then TFA treatment, purification by high-performance liquid chromatography, ion exchange treatment and freeze-drying were performed in the same manner as in Example 21 to obtain the desired compound.

Yield: 49 mg
$R_f^3$: 0.15
$[\alpha]_D$: −67.4° (c=0.5, water)
FAB mass spectrum (M+1): 640

EXAMPLE 24 pGlu-Asn-Ser-D-Pro-D-Arg-Gly-NH₂ acetate pGlu-Asn-Ser(Bu$^t$)-D-Pro-D-Arg(Mtr)-Gly-resin was prepared from 1 g of 2,4-dimethoxybenzhydrylamine resin in the same manner as in Example 21, and then TFA treatment, purification by high-performance liquid chromatography, ion exchange treatment and freeze-drying were performed in the same manner as in Example 21 to obtain the desired compound.

Yield: 62 mg
$R_f^3$: 0.16
$[\alpha]_D$: +15.3° (c=0.5, water)
FAB mass spectrum (M+1): 640

EXAMPLE 25 pGlu-Asn-Ser-Pro-Arg-OH (1) Boc-Pro-Arg(NO₂)-OBzl

To a solution of 15 g of H-Arg(NO₂)-OBzl in 250 ml of THF, 15 g of Boc-Pro-OSu was added under chilling with ice, followed by stirring for 18 hours at room temperature.

After THF was distilled off, the residue was dissolved in AcOEt. The AcOEt solution was washed successively with dilute HCl saturated aqueous NaHCO₃ solution and water, followed by drying over anhydrous Na₂SO₄.

AcOEt was distilled off. The residue was dissolved in CHCl₃-MeOH, and purified by silica-gel column chromatography to obtain the desired compound as an oily product.

Yield: 22 g
$R_f^1$: 0.61, $R_f^2$: 0.77

[α]$_D$ : −37.1° (c=1.0, DMF)

(2) Boc-Ser(Bzl)-Pro-Arg(NO$_2$)-OBzl 22 g of Boc-Pro-Arg(NO$_2$)-OBzl was placed in 110 ml of 4 N HCl-AcOEt for 30 min. at room temperature, and then the the solvent was distilled off.

After drying under reduced pressure, the residue was dissolved in 150 ml of DMF. To the solution, 9 ml of Et$_3$N, 12.8 g of Boc-Ser(Bzl)-OH, 10 g of HOBt and 9.4 g of DCC were added under chilling with ice, followed by stirring for 18 hours at room temperature.

DCUrea was removed by filtration, and DMF was distilled off. The residue was dissolved in AcOEt. Then the AcOEt solution was washed successively with dilute HCl saturated aqueous NaHCO$_3$ solution, dilute HCl and water, followed by drying over anhydrous Na$_2$SO$_4$.

AcOEt was distilled off, and the residue was treated with AcOEt to give the desired compound as a crystalline product.

Yield: 21 g
M.P.: 80°–82° C.
R$_f^1$ : 0.67, R$_f^2$ : 0.83
[α]$_D$ : −30.8° (c=1.0, DMF)

(3) Z-pGlu-Asn-Ser(Bzl)-Pro-Arg(NO$_2$)-OBzl 2.3 g of Boc-Ser(Bzl)-Pro-Arg(NO$_2$)-OBzl was placed in 10 ml of 4 N HCl-AcOEt for 30 min. at room temperature, and then the solvent was distilled off.

To the residue, 2-butanol-CH$_2$Cl$_2$ (5:1 v/v) and saturated aqueous NaHCO$_3$ solution were added. The organic portion was collected and washed with saturated aqueous NaCl solution, followed by drying over anhydrous Na$_2$SO$_4$.

The solution was distilled off, and the residue was dissolved in 20 ml of DMF. To the solution, 1.4 g of Z-pGlu-Asn-OH, 0.7 g of HOBt and 0.8 g of DCC were added under chilling with ice.

After stirring for 18 hours at room temperature, DCUrea was removed by filtration, and DMF was distilled off.

The residue was dissolved in 2-butanol CH$_2$Cl$_2$ (5:1 v/v) and then the solution was washed successively with saturated aqueous NaHCO$_3$ solution, dilute HCl saturated with NaCl and saturated aqueous NaCl solution, followed by drying over anhydrous Na$_2$SO$_4$.

The solvent was distilled off, and the residue was dissolved in CHCl$_3$-MeOH, and purified by silica-gel column chromatography to obtain the desired compound as a crystalline product.

Yield: 1.9 g
M.P. : 122°–125° C.
R$_f^1$ : 0.46, R$_f^2$ : 0.64
[α]$_D$ : −38.6° (c=1.0, DMF)

(4) pGlu-Asn-Ser-Pro-Arg-OH

A solution of 100 mg of Z-pGlu-Asn-Ser(Bzl)-Pro-Arg(NO$_2$)-OBzl in 20 ml of 80% acetic acid was stirred for 18 hours in a stream of hydrogen gas in the presence of 10% palladium-carbon.

The palladium-carbon was removed by filtration, and the solvent was distilled off. The residue was dissolved in water, and then freeze-dried.

Then the resulting product was purified by high-performance liquid chromatography at 12 ml/min. (flow rate), to 10% (B) 20 min. linear gradient (A) (mobile phase), subjected to Dowex 1×2 (acetate type) treatment and freeze-dried to obtain the desired compound.

Yield: 55 mg
R$_f^3$ : 0.18
[α]$_D$ : −85.5° (c=0.5, water)

FAB mass spectrum (M+1) : 584

EXAMPLE 26

H-Pro-Asn-Ser-Pro-Arg-OH acetate (1) Boc-Pro-Arg(NO$_2$)-OBzl

To a solution of 15 g of H-Arg(NO$_2$)-OBzl in 250 ml of THF, 15 g of Boc-Pro-OSu was added under chilling with ice, followed by stirring for 18 hours at room temperature.

After THF was distilled off, the residue was dissolved in AcOEt. The AcOEt solution was washed successively with dilute HCl saturated aqueous NaHCO$_3$ solution and water, followed by drying over anhydrous Na$_2$SO$_4$.

AcOEt was distilled off. The residue was dissolved in CHCl$_3$-MeOH, and purified by silica-gel column chromatography to obtain the desired compound as an oily product.

Yield: 22 g
R$_f^1$ : 0.61, R$_f^2$ : 0.77
[α]$_D$ : −37.1° (c=1.0, DMF)

(2) Boc-Ser (Bzl)-Pro-Arg(NO$_2$)-OBzl 22 g of Boc-Pro-Arg(NO$_2$)-OBzl was placed in 110 ml of 4 N HCl-AcOEt for 30 min. at room temperature, and then the the solvent was distilled off.

After drying under reduced pressure, the residue was dissolved in 150 ml of DMF. To the solution, 9 ml of Et$_3$N, 12.8 g of Boc-Ser(Bzl)-OH, 10 g of HOBt and 9.4 g of DCC were added under chilling with ice, followed by stirring for 18 hours at room temperature.

DCUrea was removed by filtration, and DMF was distilled off. The residue was dissolved in AcOEt. Then the AcOEt solution was washed successively with saturated aqueous NaHCO$_3$ solution, dilute HCl and water, followed by drying over anhydrous Na$_2$SO$_4$.

AcOEt was distilled off, and the residue was treated with AcOEt-ether to give the desired compound as a crystalline product.

Yield: 21 g
M.P. : 80°–82° C.
R$_f^1$ : 0.67, R$_f^2$ : 0.83
[α]$_D$ : −30.8° (c=1.0, DMF)

(3) Boc-Asn-Ser(Bzl)-Pro-Arg(NO$_2$) -OBzl 4.0 g of Boc-Ser(Bzl)-Pro-Arg(NO$_2$)-OBzl was placed in 20 ml of 4 N HCl-AcOEt for 30 min. at room temperature, and then the solvent was distilled off.

To the residue, 2-butanol-CH$_2$Cl$_2$ (5:1 v/v) and saturated aqueous NaHCO$_3$ solution was added. The organic portion was collected and washed with saturated aqueous NaCl solution, followed by drying over anhydrous Na$_2$SO$_4$.

The solution was distilled off, and the residue was dissolved in 60 ml of DMF. To the solution, 1.34 g of Boc-Asn-OH, 1.34 g of HOBt and 1.32 g of DCC were added under chilling with ice.

After stirring for 18 hours at room temperature, DCUrea was removed by filtration, and DMF was distilled off.

The residue was dissolved in 2-butanol-CH$_2$Cl$_2$ (5:1 v/v) and then the solution was washed successively with saturated aqueous NaHCO$_3$ solution, dilute HCl saturated with NaCl and saturated aqueous NaCl solution, followed by drying over anhydrous Na$_2$SO$_4$.

The solvent was distilled off, and to the residue was added AcOEt to obtain the desired compound as a crystalline product.

Yield: 4.3 g

M.P. : 186°–187° C.
$R_f^1$ : 0.55, $R_f^2$ : 0.73
$[\alpha]_D$ : −34.6° (c=1.0, DMF)

(4) Z-Pro-Asn-Ser(Bzl)-Pro-Arg(NO$_2$)-OBzl 3.5 g of Boc-Asn-Ser(Bzl)-Pro-Arg(NO$_2$)-OBzl was placed in 15 ml of 4 N HCl-AcOEt for 30 min. at room temperature, and then the solvent was distilled off.

After drying under reduced pressure, the residue was dissolved in DMF. To the solution, 0.8 ml of NMM and 1.52 g of Z-Pro-OSu were added under chilling with ice, followed by stirring for 18 hours at room temperature.

DMF was distilled off. The residue was dissolved in 2-butanol CH$_2$Cl$_2$ (5:1 v/v) and then the solution was washed successively with saturated aqueous NaHCO$_3$ solution, dilute HCl saturated with NaCl and saturated aqueous NaCl solution, followed by drying over anhydrous Na$_2$SO$_4$.

The solvent was distilled off, and the residue was purified with CHCl$_3$-methanol by silica-gel column chromatography, then was treated with ether to give the desired compound as a crystalline product.

Yield: 3.2 g
M.P. : 94°–96° C.
$R_f^1$ : 0.55, $R_f^2$ : 0.75
$[\alpha]_D$ : −45.5° (C=1.0, DMF)

(5) H-Pro-Asn-Set-Pro-Arg-OH acetate

A solution of 150 mg of Z-Pro-Asn-Ser(Bzl)-Pro-Arg(NO$_2$)-OBzl in 20 ml of 80% acetic acid was stirred for 18 hours in a stream of hydrogen gas in the presence of 10% palladium-carbon.

The palladium-carbon was removed by filtration, and the solvent was distilled off. The residue was dissolved in water, then freeze-dried.

Then the resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 96 mg
$R_f^3$ : 0.10
$[\alpha]_D$ : −91.0° (c=0.5, water)
FAB mass spectrum (M+1) : 570

EXAMPLE 27

H-Pro-Ser-Pro-Arg-OH acetate (1) Z-Pro-Ser(Bzl)-Pro-Arg(NO$_2$)-OBzl

The desired compound was prepared from 4.0 g of Boc-Ser(Bzl)-Pro-Arg(NO$_2$)-OBzl, 20 ml of 4 N HCl-AcOEt, 1 ml of NMM and 2.2 g of Z-Pro-OSu in the same manner as in Example 26-(4). The ether treatment was performed to obtain the desired compound as a crystalline product.

Yield: 4.9 g
M.P. : 72°–74° C.
$R_f^1$ : 0.66, $R_f^2$ : 0.82
$[\alpha]_D$ : −45.8° (c=1.0, DMF)

(2) H-Pro-Set-Pro-Arg-OH acetate 150 mg of Z-Pro-Ser(Bzl)-Pro-Arg(NO$_2$)-OBzl was reduced in the presence of palladium-carbon in the same manner as in Example 26-(5). The resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 75 mg
$R_f^3$ : 0.13
$[\alpha]_D$ : −97.4° (c=0.5, water)
FAB mass spectrum (M+1) : 456

EXAMPLE 28

H-Pro-Set-Pro-Arg-Gly-NH$_2$ acetate (1) Boc-Arg(NO$_2$)-Gly-NH$_2$

To a solution of 10 g of Boc-Arg(NO$_2$)-OH in 80 ml of DMF, 3.5 ml of NMM and 3.1 ml of ethyl chlorocarbonate were added under chilling with ice, followed by stirring for 15 minutes.

To the resulting solution, a mixture of 3.5 g of H-Gly-NH$_2$ hydrochloride and 3.5 ml of NMM in 20 ml of DMF was added, and then the resulting mixture was stirred for 3 hours under chilling with ice.

DMF was distilled off. The residue was dissolved in 2-butanol-CH$_2$Cl$_2$ (5:1 v/v) and then the solution was washed successively with saturated aqueous NaHCO$_3$ solution, dilute HCl saturated with NaCl and saturated NaCl aqueous solution, followed by drying over anhydrous Na$_2$SO$_4$.

The solvent was distilled off, and to the residue was added AcOEt to obtain the desired compound as a crystalline product.

Yield: 7.4 g
M.P. : 160°–162° C.
$R_f^1$ : 0.21, $R_f^2$ : 0.42
$[\alpha]_D$ : +3.2° (c=1.0, DMF)

(2) Boc-Pro-Arg(NO$_2$)-Gly-NH$_2$

The desired compound was prepared from 6.0 g of Boc-Arg(NO$_2$)-Gly-NH$_2$, 40 ml of 4 N HCl-AcOEt, 3.4 ml of Et$_3$N and 5.1 g of Boc-Pro-OSu in the same manner as in Example 26-(4).

Yield: 6.5 g
M.P. 109°–111° C.
$R_f^1$ : 0.23, $R_f^2$ : 0.45
$[\alpha]_D$ : −30.5° (c=1.0, DMF)

(3) Boc-Ser(Bzl)-Pro-Arg(NO$_2$)-Gly-NH$_2$

The desired compound was prepared from 6.0 g of Boc-Pro-Arg(NO$_2$)-Gly-NH$_2$, 35 ml of 4 N HCl-AcOEt, 1.8 ml of Et$_3$N and 5.1 g of Boc-Ser(Bzl)-OSu in the same manner as in Example 26-(4).

Yield: 6.7 g
M.P. : 109°–113° C.
$R_f^1$ : 0.32, $R_f^2$ : 0.56
$[\alpha]_D$ : −29.2° (c=1.0, DMF)

(4) Z-Pro-Ser(Bzl)-Pro-Arg(NO$_2$)-Gly-NH$_2$

The desired compound was prepared from 1.0 g of Boc-Ser(Bzl)-Pro-Arg(NO$_2$)-Gly-NH$_2$, 10 ml of 4 N HCl-AcOEt, 0.34 ml of NMM and 0.54 g of Z-Pro-OSu in the same manner as in Example 26-(4).

Yield: 0.7 g
M.P. : 108°–111° C.
$R_f^1$ : 0.34, $R_f^2$ : 0.56
$[\alpha]_D$ : −56.0° (c=1.0, DMF)

(5) H-Pro-Ser-Pro-Arg-Gly-NH$_2$ acetate 150 mg of Z-Pro-Set(Bzl)-Pro-Arg(NO$_2$)-Gly-NH$_2$ was reduced in the presence of palladium-carbon in the same manner as in Example 26-(5). The resulting product was purified by high-performance liquid chromatography at 12 ml/min. (flow rate), 0 to 10% (B) 20 min. linear gradient (A) (mobile phase), subjected to Dowex 1×2 (acetate type) treatment and freeze-dried to obtain the desired compound.

Yield: 105 mg
$R_f^3$ : 0.10
$[\alpha]_D$ : −96.7° (c=0.5, water)

FAB mass spectrum (M+1): 512

An example of pharmacological test showing the effectiveness of the peptides and the peptide derivatives of the present invention is set forth below.

Pharmacological Test: Examination on improvement effect of experimental retrograde amnesia by The effect of peptides and the peptide derivatives of the present invention on memory consolidation was evaluated by conducting one-trial passive avoidance experiment using male Wistar rats in accordance with the method described by Burbach et al., Science, vol. 221, pp. 1310–1312, 1983. The apparatus consisted of an illuminated room and a dark room, and their floors were made of stainless-steel grid. The rats placed in the illuminated room could freely enter the dark room. Upon entering the dark room the rats received an electro-shock. Retention of passive avoidance behavior to the electro-shock was determined by the measurement of a response latent period, i.e. period required for the rat experienced the electro-shock to reenter the dark room from the time on which the rat was placed in the illuminated room after predetermined intervals.

The rats received an electro-shock (0.5 mA) after one hour from the administration of the peptides of the present invention or a physiological saline solution. Immediately after receiving the electro-shock, the rats were treated with 2.7 to 3.0 mG/kg of cycloheximide or the saline solution by subcutaneous injection. At 48 hours after the administration was made, memory retention of the rats were tested. The rats administered with only the physiological saline solution showed the response latent period of approx. 300 seconds, and those rats of control Group administered with cycloheximide alone showed the response latent period of approx. 50 seconds, which revealed retrograde amnesia.

The average response latent period of rats administered with each peptide of the present invention was compared with that of the control group. Six to eight rats were used for each group to be tested. The response latent period was measured up to a maxime of 600 seconds.

The dose and the effect (the ratio of response latent period of each group to that of the control Groups, shown as %) of the peptides obtained in each example are set forth in Table 1.

TABLE 1

| Compound | Dose (ng/kg) | Effect (%) |
|---|---|---|
| Example 5 | 1 | 298 |
| Example 6 | 1 | 239 |
| Example 9 | 1 | 460 |
| Example 12 | 1 | 235 |
| Example 16 | 1 | 251 |
| Example 17 | 1 | 365 |
| Example 21 | 0.1 | 353 |
| Example 27 | 0.1 | 213 |

As readily apparent from the above experimental results, the peptides and the peptide derivatives of the invention showed superior effect on improving retrograde amnesia.

Preparation examples of pharmaceuticals containing the peptide derivatives of the present invention are shown below.

Preparation Example 1 (Injection)

To 100 ml of a distilled water for injection were added 0.1 mg of the peptide derivative obtained in Example 1 and 0.9 g of NaCl to prepare an aqueous solution whose pH was adjusted to 6.0 to 8.0 with NaOH. The solution was filtered under sterile condition, and the filtrate was filled up into 1 ml ampul. The ampul was fused to seal under sterile condition by heating to prepare an agent for injection.

With respect to each of the peptides obtained in Examples 7, 12, 15, 21 and 26, the above-described procedure was repeated to prepare agents for injection containing each peptide.

Preparation Example 2 (Freeze-Dried Agent)

To 100 ml of a distilled water for injection were added 5 mg of the peptide derivative obtained in Example 1 and 5 g of D-mannitol to prepare an aqueous solution whose pH was adjusted to 6.0 to 8.0 with a phosphate buffer. The solution was filtered under sterile condition, and the filtrate was divided into a plurality of 1 ml vials. The divided portions were freeze-dried to prepare a freeze-dried agent for injection.

With respect to each of the peptides obtained in Examples 7, 12, 15, 21 and 26, the above-described procedure was repeated to prepare freeze-dried agents for injection containing each peptide.

Preparation Example 3 (Collunarium)

To 100 ml of a physiological saline solution was added 10 mg of the peptide derivative obtained in Example 1. The pH of the mixture was adjusted to 3.0 to 6.0 with a citric acid buffer to prepare a collunarium which contains 50 μg of the peptide of the invention in a dose of 0.5 ml.

With respect to each of the peptides obtained in Examples 7, 12, 15, 21 and 26, the above-described procedure was repeated to prepare collunariums containing each peptide.

Preparation Example 4 (Suppository)

To 98.5 g of hard fat (triglyceride of saturated fatty acid) was added 0.5 g of egg york lecithin. The mixture was melted at temperature of 40° to 45° C. and to the melted mixture was added under stirring a solution of 5 mg of the peptide derivative obtained in Example 1 in 1 g of PEG 400. The resulting dispersion (1 g) was filled into the mold for suppository. The content was removed from the mold after being caked to prepare a suppository.

With respect to each of the peptides obtained in Examples 7, 12, 15, 21 and 26, the above-described procedure was repeated to prepare suppositories containing each peptide.

We claim:

1. A peptide selected from the group consisting of:

H—Asn—Ser—Pro—Arg—OH
H—Asn—Thr—Pro—Arg—OH
H—Asn—Ala—Pro—Arg—OH
H—Asn—Ser—D—Pro—Arg—OH
H—Asn—Ser—Pro—Arg—Gly—NH$_2$
H—Asn—Ser—Pip—Arg—OH
H—Pro—Ser—Pip—Arg—OH
H—Pro—Asn—Ser—Pip—Arg—OH

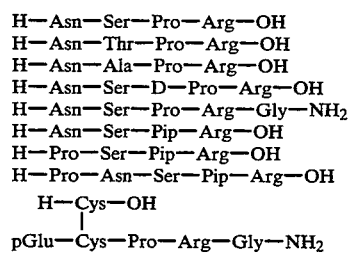

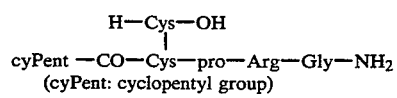

(cyPent: cyclopentyl group)

-continued
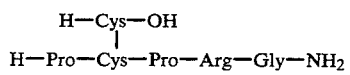
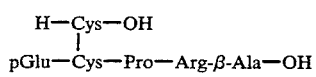
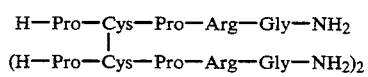
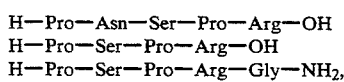
and a pharmaceutically acceptable salt thereof.
2. A peptide selected from the group consisting of:
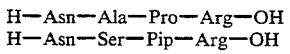
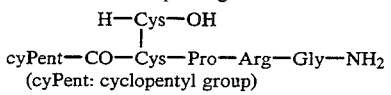
(cyPent: cyclopentyl group)
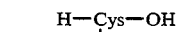
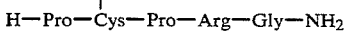
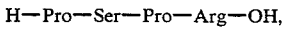
and a pharmaceutically acceptable salt thereof.
* * * * *